United States Patent [19]
Eaton et al.

[11] Patent Number: 5,954,654
[45] Date of Patent: Sep. 21, 1999

[54] STEERING MECHANISM AND STEERING LINE FOR A CATHETER-MOUNTED ULTRASONIC TRANSDUCER

[75] Inventors: John W. Eaton, Palo Alto; David J. Rosa, San Jose; Vaughn Marian, Saratoga; Jay Plugge, Sunnyvale, all of Calif.

[73] Assignee: Acuson Corporation, Mountain View, Calif.

[21] Appl. No.: 08/792,897

[22] Filed: Jan. 31, 1997

[51] Int. Cl.$^6$ .............................. A61B 8/12; A61M 37/00
[52] U.S. Cl. ............................................. 600/462; 600/459
[58] Field of Search ................................... 600/446, 462, 600/459; 604/95, 280, 282; 606/41; 607/122

[56] References Cited

U.S. PATENT DOCUMENTS

| | | |
|---|---|---|
| 4,207,873 | 6/1980 | Kruy . |
| 4,435,614 | 3/1984 | McAusland . |
| 4,474,174 | 10/1984 | Petruzzi . |
| 4,605,009 | 8/1986 | Pourcelot et al. . |
| 4,794,931 | 1/1989 | Yock . |
| 4,841,976 | 6/1989 | Packard et al. ..................... 606/164 |
| 4,951,677 | 8/1990 | Crowley et al. . |
| 5,275,151 | 1/1994 | Shockey et al. . |
| 5,322,064 | 6/1994 | Lundquist . |
| 5,336,182 | 8/1994 | Lundquist et al. . |
| 5,345,940 | 9/1994 | Seward et al. . |
| 5,359,994 | 11/1994 | Krauter et al. . |
| 5,364,352 | 11/1994 | Cimino et al. . |
| 5,368,037 | 11/1994 | Eberle et al. . |
| 5,383,852 | 1/1995 | Stevens-Wright . |
| 5,383,923 | 1/1995 | Webster, Jr. . |
| 5,385,148 | 1/1995 | Lesh et al. . |
| 5,395,327 | 3/1995 | Lundquist et al. . |
| 5,395,329 | 3/1995 | Fleischhackor et al. . |
| 5,397,304 | 3/1995 | Truckai . |
| 5,398,689 | 3/1995 | Connor et al. . |
| 5,431,168 | 7/1995 | Webster, Jr. . |
| 5,439,006 | 8/1995 | Brennen et al. . |
| 5,453,575 | 9/1995 | O'Donnell et al. . |
| 5,456,258 | 10/1995 | Kondo et al. . |
| 5,462,527 | 10/1995 | Stevens-Wright et al. . |
| 5,479,930 | 1/1996 | Gruner et al. . |
| 5,489,270 | 2/1996 | van Erp ..................................... 604/95 |
| 5,492,126 | 2/1996 | Hennige et al. . |
| 5,512,035 | 4/1996 | Konstorum et al. . |
| 5,514,115 | 5/1996 | Frantzen et al. . |
| 5,527,279 | 6/1996 | Imran ......................................... 606/41 |
| 5,531,685 | 7/1996 | Hemmer et al. . |
| 5,571,085 | 11/1996 | Accisano, III . |
| 5,662,606 | 9/1997 | Cimino et al. ............................. 604/95 |
| 5,722,402 | 3/1998 | Swanson et al. . |
| 5,722,403 | 3/1998 | McGee et al. . |

*Primary Examiner*—Francis J. Jaworski
*Attorney, Agent, or Firm*—Brinks Hofer Gilson & Lione

[57] ABSTRACT

A steering mechanism for an ultrasonic transducer assembly includes a housing having a longitudinal axis that extends generally parallel to the proximal end of a catheter. An annular steering ring is mounted to the housing for rotation about the longitudinal axis, and a steering hub is mounted for rotation in the housing and coupled to the steering ring such that rotation of the steering ring with respect to the housing causes rotation of the steering hub. A steering line is secured adjacent the steering hub and extends to the distal end of the catheter such that rotation of the steering hub alters the effective length of the steering line to steer the distal end. The steering line is preferably formed of a stranded polymer such as a gel spun polyethylene.

23 Claims, 4 Drawing Sheets

STEERING MECHANISM AND STEERING LINE FOR A CATHETER-MOUNTED ULTRASONIC TRANSDUCER

BACKGROUND OF THE INVENTION

This invention relates to steering mechanisms and steering lines for catheter-mounted ultrasonic transducers.

Catheter-mounted ultrasonic transducers are known to the art, as described for example in U.S. Pat. No. 4,794,931 and 5,368,037. These catheter-mounted transducers are single use, disposable devices which provide a radial image format either by means of a radial phased array or a rotating crystal. These devices do not include any mechanism for steering or articulating the tip of the catheter. Because the catheter tip cannot be steered, it is in general not possible to position the transducer optimally to obtain different views of the tissue or structure being imaged.

Catheters other than ultrasonic imaging catheters currently exist which have articulating tips. One typical steering mechanism for such a catheter uses a knob which rotates about an axis perpendicular to the length of the catheter. As the user rotates the knob clockwise or counterclockwise, the tip of the catheter will articulate either up and down, or left and right. In addition to manipulating the catheter tip with the knob, the catheter is generally rotated within the vessel by rotating the control housing. Such rotation of the control housing causes the knob to rotate as well as the catheter, and can place the knob in an relatively inaccessible position for the user. Awkward positioning of the steering knob can make manipulating the catheter tip difficult.

Accisano U.S. Pat. No. 5,571,085 and Fleischhackor U.S. Pat. No. 5,395,329 disclose control handles for steerable catheters which utilize a rotating collar to move a slide longitudinally in the catheter handle. Steering lines are connected to the slide such that reciprocation of the slide steers the distal tip of the catheter. This arrangement provides the advantage of a steering actuator which extends around the complete circumference of the handle and rotates about the longitudinal axis of the handle.

SUMMARY OF THE INVENTION

The present invention is directed to an improved steering mechanism for a catheter-mounted ultrasonic transducer assembly, and to an improved steering line.

According to a first aspect of this invention, a steering mechanism is provided for an ultrasonic transducer assembly of the type comprising an elongated conduit comprising a distal end portion and a proximal end portion, a plurality of ultrasonic transducer elements carried by the conduit adjacent the distal end portion, and at least one steering line carried by the conduit.

The steering mechanism comprises a housing defining a longitudinal axis extending generally parallel to the proximal portion of the conduit, an actuator such as a steering ring is carried by the housing for rotation about the longitudinal axis, and a steering hub mounted for rotation in the housing and coupled to the actuator such that rotation of the actuator with respect to the housing about the longitudinal axis causes rotation of the steering hub. The steering line is secured adjacent the steering hub such that rotation of the steering hub alters the effective length of the steering line to steer the distal end of the conduit.

This aspect of the invention combines the advantage of an actuator that rotates about the longitudinal axis of the housing with a steering hub that is connected to the steering line and also rotates in the housing.

According to another aspect of this invention, a steerable, catheter-mounted ultrasonic transducer assembly is provided comprising an elongated conduit and a plurality of transducer elements as described above. A steering mechanism is coupled to the proximal portion of the conduit, and at least one steering line interconnects the steering mechanism and the distal end portion of the conduit. According to this aspect of the invention, the steering line comprises a stranded polymer such as a gel spun polyethylene. The use of stranded polymer for the steering line provides advantages in terms of low stretch or elongation, high tensile strength, and good wear characteristics.

Though these two aspects of the invention are preferably used together as described below, they can if desired be used independently of one another. For example, the steering mechanism of this invention can be used with conventional, metal steering lines, and conversely the steering lines of this invention can be used with conventional steering mechanisms.

DETAILED DESCRIPTION OF THE PRESENTLY PREFERRED EMBODIMENTS

Figures 1, 3:
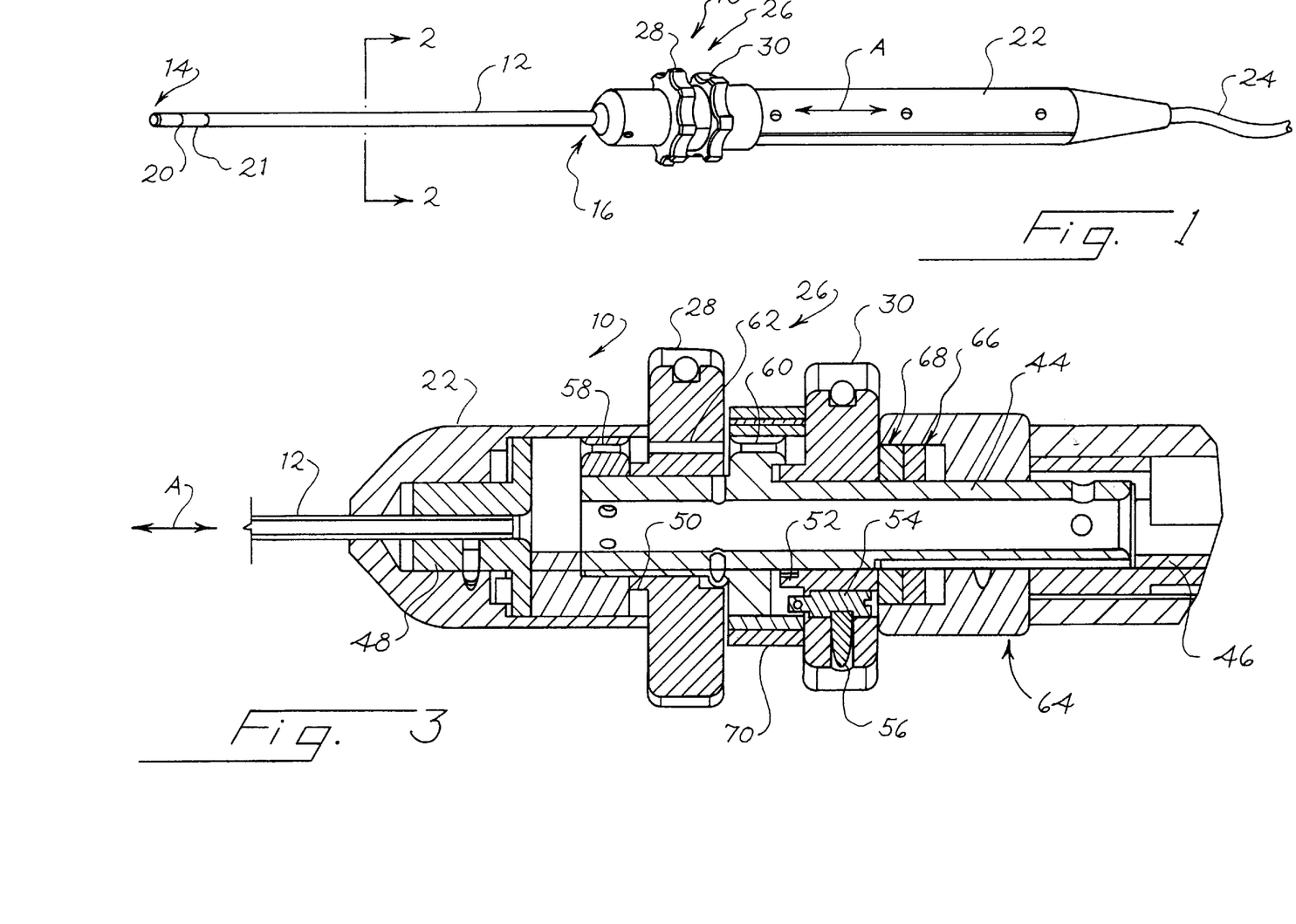
FIG. 1 is a perspective view of a catheter-mounted ultrasonic transducer assembly that comprises the first preferred embodiment of this invention.
FIG. 3 is a cross-sectional view of a portion of the handle of the embodiment of FIG. 1.

Turning now to the drawings, FIG. 1 shows a side view of a transducer assembly 10 that incorporates a preferred embodiment of this invention. The transducer assembly 10 includes an elongated catheter 12 having a distal end 14 and a proximal end 16. A linear array of transducer elements 20 is carried by the distal end 14 of the catheter 12. The transducer elements 20 can be arranged in a linear or a curvilinear phased array, depending upon the application. The portion of the catheter 12 immediately proximal to the transducer elements 20 is formed of a lower hardness polymer enabling it to articulate or steer in any of four directions (up/down and left/right).

The catheter 12 is mounted in a housing 22 that is connected by a cable 24 to a medical diagnostic ultrasonic imaging system (not shown). The housing 22 includes a steering mechanism 26 that in turn includes first and second actuators, which in this embodiment take the form of steering rings 28,30. The first steering ring 28, when rotated, causes the distal end 14 to move in a first plane, and the second steering ring 30, when rotated, causes the distal end 14 to articulate in a second plane, transverse to the first plane. As shown in FIG. 1, the first and second steering rings 28,30 extend circumferentially around the housing 22, and each pivots about an axis A which is parallel to the centerline of the catheter 12 adjacent the proximal end 16.

Figure 2:
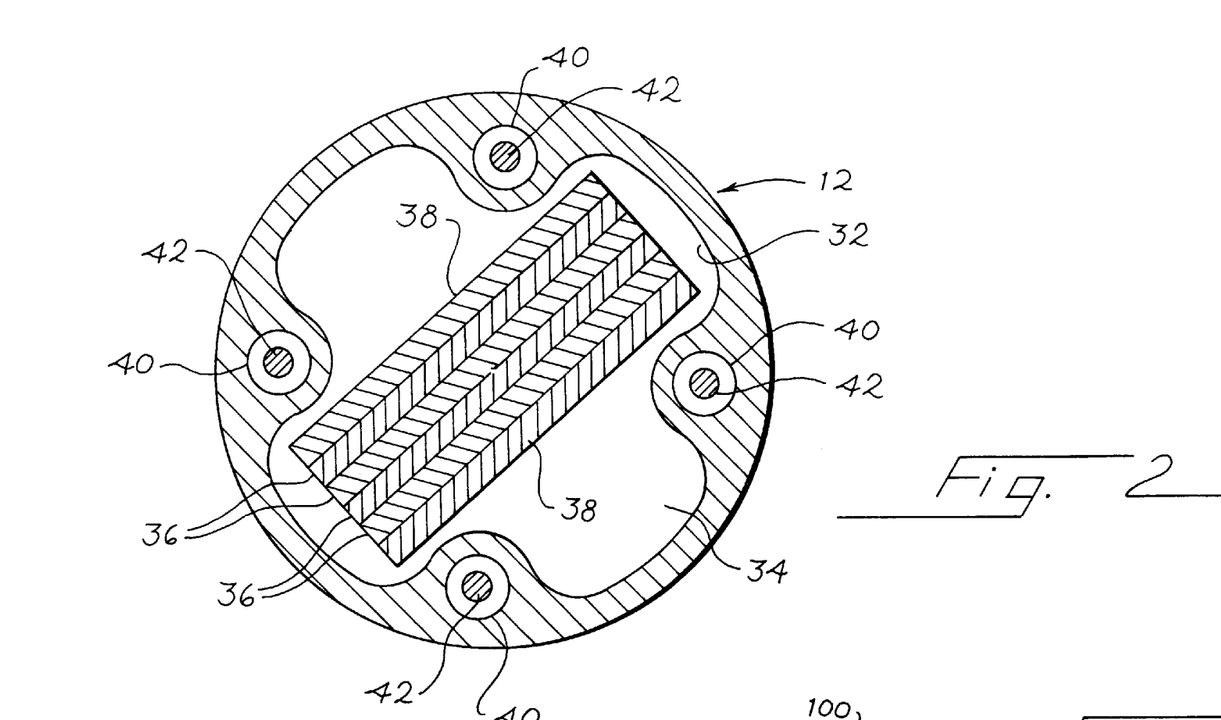
FIG. 2 is a cross-sectional view taken along line 2—2 of FIG. 1.

Turning now to FIG. 2, the catheter 12 includes a conduit 32 that defines a central lumen 34. The central lumen 34 carries a stack of flexible circuit strips 36, 38. The flexible circuit strips 36 carry transmit signals to the transducer elements and receive signals from the transducer elements. The flexible circuit strips also include ground return paths. The flexible circuit strips 38 are provided with uninterrupted copper shields extending over their entire width and length in order to reduce EMI interference to and from the catheter 12. These shields are preferably not connected to the transducer elements.

The conduit 32 also defines four smaller lumens 40, and each of the lumens 40 carries a respective steering line 42. In this embodiment, the steering lines 42 are formed in diametrically opposed pairs, and the steering lines 42 within each pair are continuous from the steering mechanism 26 to the proximal portion of the transducer elements 20 (FIG. 1). The steering line makes a reverse curve at this point and is secured in place to the distal end of a short segment 21 of conduit (approximately 1.5 inches in length) that is integral with the main conduit and is of substantially lower hardness than the body of the catheter. As described below, by increasing tension on one steering line while relieving tension on the diametrically opposed steering line, this lower hardness portion will be preferentially compressed and can bend or be steered in either of two transverse planes. As used herein, the term "set of steering lines" means one or more steering lines.

Figure 5:
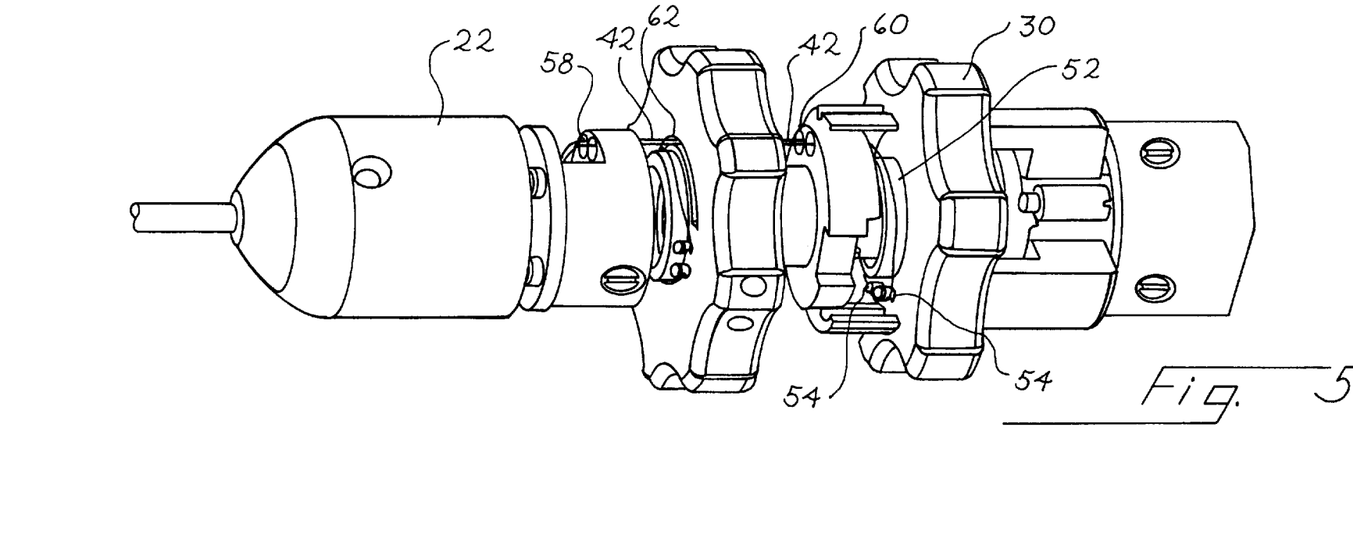

FIG. 3 shows a cross-sectional view of the steering mechanism 26. As shown in FIG. 3, the steering mechanism 26 includes a central shaft 44 that is fixed in place to the proximal portion 46 of the housing 22. This shaft 44 supports at its forward end 48 the catheter 12. The shaft 44 also supports the first and second steering rings 28,30 for rotation about the axis A. Each of the steering rings 28,30 defines an annular shape which is accessible around the complete circumference of the housing 22. The first and second steering rings 28,30 support first and second steering hubs 50,52 respectively. In this embodiment the steering hubs 50,52 are integrally formed with the steering rings 28,30, respectively, and rotate with them as a unit. Each of the steering rings 28,30 also supports a pair of anchor pins 54 (FIG. 5). Each anchor pin 54 is mounted for rotation in the respective steering ring 28,30, and can be rotated with a conventional screwdriver. A set screw 56 can be used to lock the anchor pin 54 against undesired rotation after it has been properly adjusted (FIG. 3).

Also as shown in FIG. 3, the shaft 44 fixedly supports first and second guides 58,60. Each of the guides in this embodiment is formed as a passageway oriented longitudinally, parallel to the axis A and disposed radially outwardly from and adjacent to the respective steering hub 50,52. FIG. 3 also shows a slot 62 formed in the steering ring 28 and aligned with the guides 60.

Other elements of the steering mechanism 26 shown in FIG. 3 include a brake knob 64 which is mounted for rotation on the shaft 44. Rotation of the brake knob 64 causes pins (not shown) mounted in the knob to slide along a ramp washer 66. The ramp washer is pushed forwardly (distally) and compresses an elastomeric washer 68 against the second steering ring 30. A collar 70 is positioned between the first and second steering rings 28,30. When the brake knob 64 and pins are rotated in the opposite direction, pressure is removed from the washer 68 and the collar 70, and the steering rings 28,30 can be rotated independently of one another to steer the catheter 12 as desired. When it is desired to lock the steering rings 28,30 in position, the brake knob 64 is rotated to press the washer 68 against the steering ring 30. This pressure causes the steering ring 30 to press the collar 70 against the first steering ring 28, thereby immobilizing both steering rings 28, 30.

Figure 4:
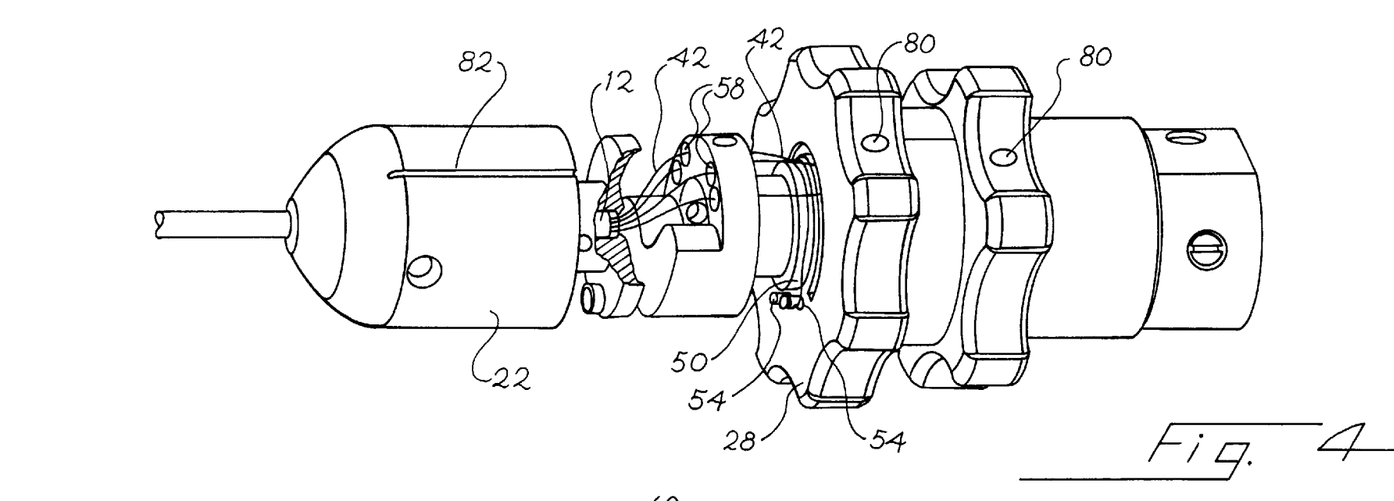
FIGS. 4 and 5 are two exploded, perspective views of the embodiment of FIG. 1.

In FIG. 3 the steering lines 44 have been deleted for clarity. FIG. 4 is a partially exploded perspective view showing the manner in which the steering lines 42 are passed from the catheter 12 via the guides 58. Two of the steering lines 42 that are diametrically opposed in the catheter 12 pass from the guides 58 around opposite sides of the steering hub 50 and are anchored on the respective anchor pins 54 of the steering ring 28 (FIG. 5).

As shown in FIG. 5, the other two of the steering lines 42 pass from the guides 58 through the arcuate slot 62 and the guides 60 to the second steering hub 52. These steering lines 42 wrap around opposite sides of the steering hub 52 and are then anchored to respective ones of the anchor pins 54 on the steering ring 30.

The steering mechanism shown in FIGS. 3–5 allows each diametrically opposed pair of steering lines 42 to be controlled by a respective one of the steering rings 28,30. When the respective steering ring 28,30 is rotated, one of the corresponding pair of steering lines 42 is increased in effective length, and the other is decreased in effective length. This causes the distal end 14 of the catheter 12 to be steered in the respective plane. Because the steering rings 28,30 extend in an uninterrupted fashion around the circumference of the housing 22, the steering rings 28,30 are always accessible to the user, regardless of the rotational position of the housing 22. Because the steering hubs 50,52 rotate around the same axis as the steering rings 28,30, the steering mechanism is relatively simple in construction and operates substantially without play. As best shown in FIG. 4, indicating bumps 80 protrude from the steering rings. When the steering rings are rotated to align the indicating bumps 80 with a slot 82 on the housing 22, the steering mechanism is placed in a neutral position, in which the tip is not deflected. The bumps 80 and slot 82 act as physical markers and may be raised, lowered, or assymetrically shaped with respect to the adjacent surface.

During setup, the anchor pins 54 are rotated to shorten or lengthen the respective steering lines 42. Once properly adjusted, the anchor pins 54 are immobilized against further motion with the set screws 56 (FIG. 3).

In this embodiment the steering lines 42 are preferably formed of a flexible, substantially inextensible polymer such as gel spun polyethylene. Such a stranded polymer is well suited for use in this application because of its excellent flexibility, wear resistance, and resistance to stretching. Since the steering line traverses through guides and around the steering hub, it must be flexible. It must also have enough tensile strength to articulate the tip without breaking. A line with low stretch prevents the steering ring from developing excessive backlash over repeated uses. And the line must be resistant to fraying. Stranded metallic wire and Kevlar® line have been tried but are prone to fraying and breaking after minimal cycling.

Figure 6:
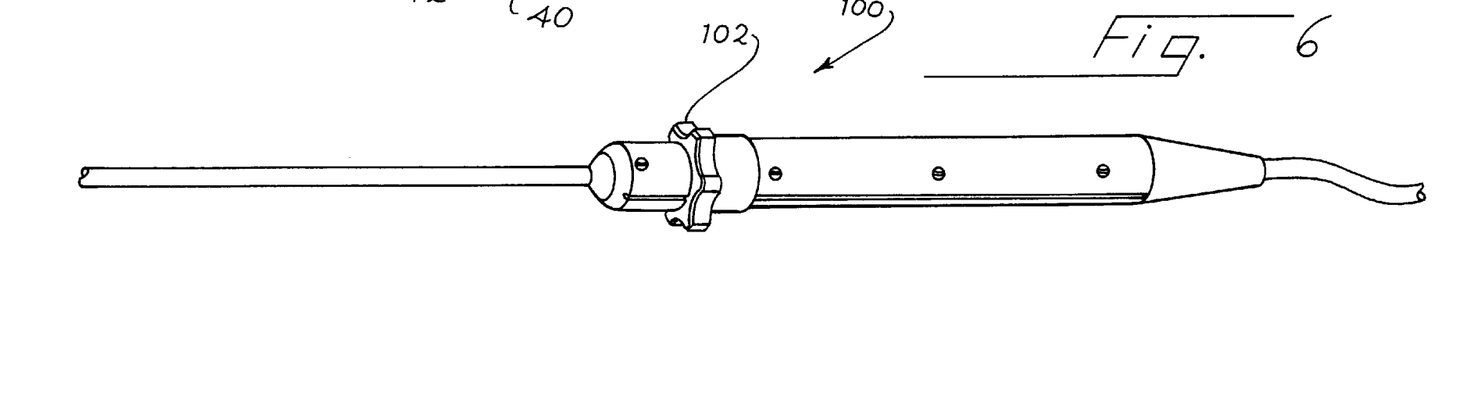
FIG. 6 is a side view of a second preferred embodiment of this invention.

FIG. 6 shows a side view of a transducer assembly 100 which incorporates a second preferred embodiment of this invention. The transducer assembly 100 is essentially identical to the transducer assembly 10 described above except that only a single steering ring 102 is provided. The transducer assembly 100 can be steered only in a single plane with the steering ring 102, but this arrangement is suitable for many applications.

Figure 7:
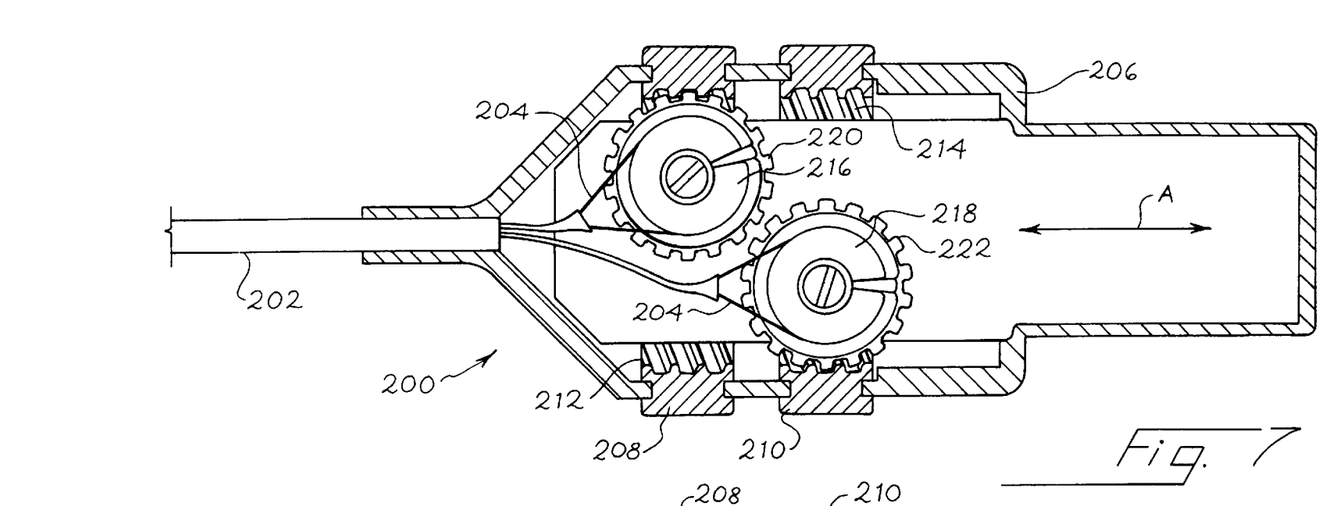
FIG. 7 is a longitudinal sectional view of a third preferred embodiment of this invention.
Figure 8:
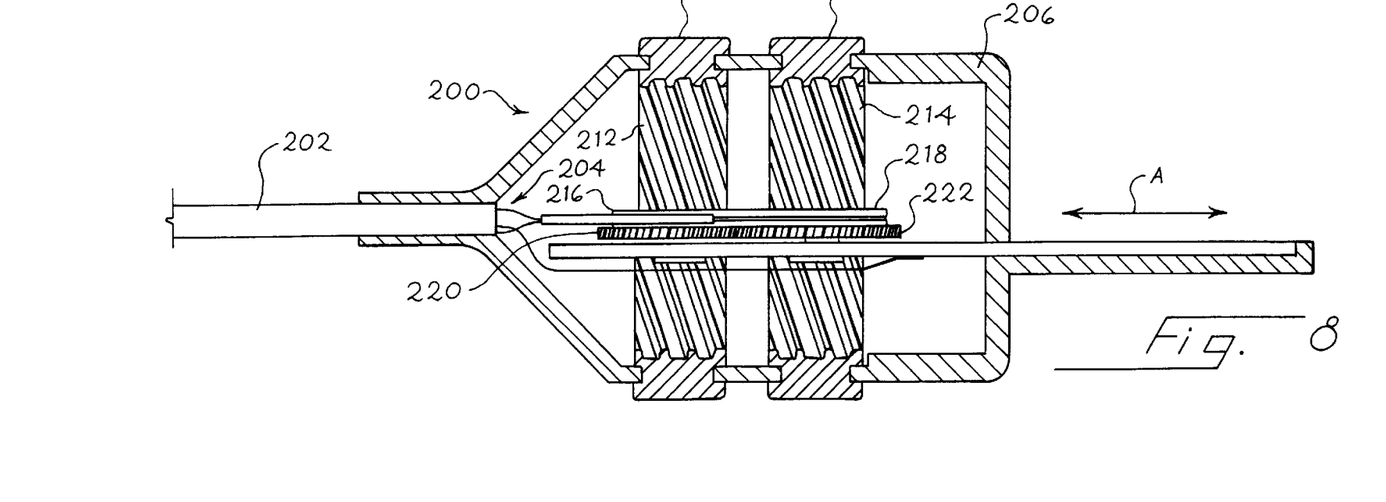
FIG. 8 is a longitudinal sectional view of the embodiment of FIG. 7, taken in a plane perpendicular to that of FIG. 7.

FIGS. 7 and 8 are sectional views of a transducer assembly 200 that incorporates a third preferred embodiment of this invention. The transducer assembly 200 includes a catheter 202 which may be identical to the catheter 12 described above, and which houses four steering lines 204.

As best shown in FIG. 7, the transducer assembly 200 includes a housing 206 that supports two annular actuators or steering rings 208,210 for rotation about an axis A which corresponds to the centerline of the catheter 202. Each of the steering rings 208,210 is provided with an internal helical gear 212,214, respectively.

As shown in FIG. 7, the transducer assembly 200 includes first and second steering hubs 216,218, each mounted for rotation about a respective axis oriented transversely to the axis A. Each steering hub 216,218 includes a respective outer helical gear 220,222, and the gears 220,222 are in driving engagement with the gears 212,214, respectively.

As before, the steering lines 204 are divided into two pairs, each disposed in diametrically opposed lumens of the catheter 202. The steering lines 204 of each pair are wrapped in opposing directions around and anchored in place to the respective steering hub 216,218. In use, the catheter 202 can be steered in either of two transverse planes by appropriately rotating the steering rings 208,210. Rotation of the steering ring 208,210 causes corresponding rotation of the respective steering hub 216,218. As before, rotation of the steering hub 216,218 increases the effective length of one steering line and decreases the effective length of the other steering line in the respective pair in order to steer the distal end of the catheter 202.

Because of the mechanical advantage between the steering rings, 208 and 210, and the steering hubs 220 and 222, generated by the design of the helical surfaces, and because of the friction between the steering rings and the hubs, and between the steering rings and the housing 206, the catheter will retain its adjusted configuration, even when the operator removes his hands from the steering rings. The retention of an adjusted configuration without operator attention is a desirable feature of this design.

Simply by way of example, the following materials can be used with this invention. The steering lines 42, 204 can be formed of a stranded polymer such as that sold under the tradename Spectra® in a thickness of about 0.006 inch. For example the material sold by Cabella's as Spiderwire™ (6# test diameter, 30# test strength) has been found suitable. In addition, the catheter may be formed as described in U.S. patent application Ser. No. 08/791,598, and the flexible circuits of the catheter may be fabricated as described in U.S. Pat. application Ser. No. 08/791,601, both assigned to the assignee of the present invention. The entire disclosures of both of these patent applications are hereby incorporated by reference.

From the foregoing, it should be apparent that several embodiments have been described of steering mechanisms that utilize a steering ring that rotates around the longitudinal axis of the proximal end of the catheter. In each case the steering mechanism converts angular displacement of the steering ring into linear displacement of the steering lines that run the length of the catheter from the proximal to the distal end. Because the steering rings extend completely around the housing, they remain accessible to the user, regardless of the rotational position of the housing. Also, an improved material for steering lines has been disclosed which provides excellent operating characteristics.

Of course, it should be understood that a wide range of changes and modifications can be made to the preferred embodiments described above. For example, the steering line of this invention may be used with any suitable type of steering mechanism. In addition, other steering lines (stranded or unstranded, using other materials such as metal and other polymers) are also possible, and a steering line may be formed by joining two or more sections of differing materials by tying or bonding. For example, a steering line can comprise a gel spun polyethylene section jointed to a Kevlar® section, or a gel spun polyethylene section jointed to a stranded metallic wire section. Additionally, other gear arrangements can be used in the steering mechanism. It should be clearly understood that the foregoing detailed description has described only a few of the many forms that the present invention can take. It is only the following claims, including all equivalents, that are intended to define the scope of this invention.

We claim:

1. A steering mechanism for an ultrasonic transducer assembly of the type comprising: an elongated conduit comprising a distal end portion and a proximal end portion; a plurality of ultrasonic transducer elements carried by the conduit adjacent the distal end portion; and a set of steering lines comprising a first steering line carried by the conduit; said steering mechanism comprising:

a housing defining a longitudinal axis extending generally parallel to the proximal portion of the conduit;

an actuator mounted to the housing for rotation about the longitudinal axis;

a steering hub mounted for rotation in the housing and coupled to the actuator such that rotation of the actuator with respect to the housing about the axis causes rotation of the steering hub;

said steering hub being adapted to have said first steering line secured adjacent thereto such that rotation of the steering hub alters effective length of the first steering line to steer the distal end.

2. The invention of claim 1 wherein the actuator comprises an internal gear, and wherein the steering hub comprises a gear wheel engaged with the internal gear.

3. The invention of claim 2 wherein said gear wheel is mounted for rotation about a second axis oriented substantially transverse to the longitudinal axis.

4. The invention of claim 1 wherein the steering hub rotates in unison with the actuator about the longitudinal axis.

5. The invention of claim 1 wherein the actuator is annular in shape, and wherein the actuator is accessible to a user around a complete circumference of the housing.

6. The invention of claim 1 wherein the set of steering lines additionally comprises a second steering line, wherein said steering hub is adapted to have said first and second steering lines wrap in opposite directions at least partially around said hub and to have said steering lines secured thereto.

7. The invention of claim 1 wherein internal friction between the actuator and the steering hub and between the actuator and the housing cause the conduit to retain its adjusted configuration without operator attention.

8. A steering mechanism for an ultrasonic transducer assembly of the type comprising: an elongated conduit comprising a distal end portion and a proximal end portion; a plurality of ultrasonic transducer elements carried by the conduit adjacent the distal end portion; and a set of steering lines comprising a first steering line carried by the conduit; said steering mechanism comprising:

a housing defining a longitudinal axis extending generally parallel to the proximal position of the conduit;

a steering ring mounted for rotation about the longitudinal axis, said steering ring accessible to a user around a complete circumference of the housing;

a steering hub carried by the steering ring for rotation about the longitudinal axis;

a guide carried by the housing adjacent the steering hub, said guide positioned radially outwardly of the steering hub and extending longitudinally of the housing;

said guide being adapted to have said first steering line pass therethrough and said steering hub being adapted to have said first steering line secured adjacent thereto such that rotation of the steering hub alters the effective length of the first steering line to steer the distal end.

9. The invention of claim 8 wherein the set of steering lines additionally comprises a second steering line, wherein said steering hub is adapted to have said first and second steering lines wrap in opposite directions at least partially around said hub and to have said steering lines secured adjacent thereto.

10. The invention of claim 8 wherein the set of steering lines additionally comprises a second steering line, and wherein the steering mechanism further comprises:

a second steering ring mounted to the housing for rotation about the longitudinal axis, said second steering ring accessible to a user around a complete circumference of the housing;

a second steering hub carried by the second steering ring for rotation about the longitudinal axis;

a second guide carried by the housing adjacent the second steering hub, said second guide positioned radially outwardly of the steering hub and extending longitudinally of the housing;

said second guide being adapted to have said second steering line pass therethrough, said second steering hub being adapted to have said second steering line secured adjacent thereto alters effective length of the second steering line to steer the distal end;

said first steering ring being adapted to have said second steering line pass therethrough.

11. The invention of claim 10 further comprising a brake control element carried by the housing and coupled to the first and second steering rings such that rotation of the brake control element applies friction to both of the first and second steering rings to hold the steering rings in a selected position with respect to the housing.

12. A steering mechanism for an ultrasonic transducer assembly of the type comprising: an elongated conduit comprising a distal end portion and a proximal end portion; a plurality of ultrasonic transducer elements carried by the conduit adjacent the distal end portion; and a set of steering lines comprising a first steering line carried by the conduit; said steering mechanism comprising:

a housing defining a longitudinal axis extending generally parallel to the proximal portion of the conduit;

a steering ring mounted to the housing for rotation about the longitudinal axis, said steering ring accessible to a user around a complete circumference of the housing, said steering ring comprising an internal gear;

a steering hub mounted for rotation in the housing about a second axis oriented transversely to the longitudinal axis, said steering hub comprising a gear wheel comprising gear teeth engaged with the internal gear such that rotation of the steering ring about the longitudinal axis causes the steering hub to rotate about the transverse axis;

said steering hub being adapted to have said first steering line secured adjacent thereto such that rotation of the steering hub alters effective length of the first steering line to steer the distal end.

13. The invention of claim 12 wherein the set of steering lines additionally comprises a second steering line, wherein said steering hub is adapted to have said first and second steering line wrap in opposite directions at least partially therearound, and wherein the steering hub is further adapted to have said first and second steering lines secured thereto.

14. The invention of claim 12 wherein the set of steering lines additionally comprises a second steering line, and wherein the steering mechanism further comprises:

a second steering ring mounted to the housing for rotation about the longitudinal axis, said second steering ring accessible to a user around a complete circumference of the housing, said second steering ring comprising a second internal gear;

a second steering hub mounted for rotation in the housing about an additional axis oriented transversely to the longitudinal axis, said second steering hub comprising a second gear wheel comprising gear teeth engaged with the second internal gear such that rotation of the second steering ring about the longitudinal axis causes the second steering hub to rotate about the additional transverse axis;

said second steering hub being adapted to have said second steering line secured thereto alters effective length of the second steering line to steer the distal end.

15. The invention of claim 1 or 8 or 12 wherein the steering line comprises a stranded polymer.

16. The invention of claim 15 wherein the stranded polymer comprises a gel spun polyethylene.

17. The invention of claim 1 further comprising a first physical marker on the housing and a second physical marker on the actuator, said markers positioned such that the distal end portion is in a neutral position when the markers are aligned.

18. The invention of claim 8 or 12 further comprising a first physical marker on the housing and a second physical marker on the steering ring, said markers positioned such that the distal end portion is in a neutral position when the markers are aligned.

19. In a steerable, catheter-mounted ultrasonic transducer assembly comprising: an elongated conduit comprising a distal end portion and a proximal end portion; a plurality of ultrasonic transducer elements carried by the conduit adjacent the distal end portion; and a steering mechanism coupled to the proximal end portion of the conduit; the improvement comprising:

at least one first steering line interconnecting the steering mechanism and the distal end portion of the conduit, said steering line comprising a stranded polymer.

20. The invention of claim 19 wherein the stranded polymer comprises a gel spun polyethylene.

21. The invention of claim 1 or 8 or 12 or 19 wherein the first steering line comprises first and second sections that are joined together, said first and second sections comprising differing materials.

22. The invention of claim 21 wherein the first section comprises a gel spun polyethylene and the second section comprises Kevlar®.

23. The invention of claim 21 wherein the first section comprises a gel spun polyethylene and the second section comprises stranded metallic wire.

* * * * *

UNITED STATES PATENT AND TRADEMARK OFFICE
CERTIFICATE OF CORRECTION

PATENT NO. : 5,954,654
DATED : September 21, 1999
INVENTOR(S) : John W. Eaton et al.      Page 1 of 2

It is certified that error appears in the above-indentified patent and that said Letters Patent is hereby corrected as shown below:

On the Title Page

In column 1, after line 7, under "U.S. PATENT DOCUMENTS", insert

--5,207,225   5/1993   Oaks et al.--;

after line 11, insert

--5,351,692   10/1994   Dow et al.--.

In column 2, after line 4, insert

--5,402,793   4/1995   Gruner et al.
  5,413,107   5/1995   Oakley et al.--

In column 1, line 28, change "an" to --a--.

UNITED STATES PATENT AND TRADEMARK OFFICE
CERTIFICATE OF CORRECTION

PATENT NO. : 5,954,654
DATED : September 21, 1999
INVENTOR(S) : John W. Eaton et al.

It is certified that error appears in the above-indentified patent and that said Letters Patent is hereby corrected as shown below:

In claim 13, line 4, change "line" to --lines--.

In claim 14, line 18, after "secured" insert --adjacent--.

Signed and Sealed this

First Day of May, 2001

Attest:

NICHOLAS P. GODICI

Attesting Officer     Acting Director of the United States Patent and Trademark Office